United States Patent [19]

Garzia et al.

[11] Patent Number: 4,753,937
[45] Date of Patent: Jun. 28, 1988

[54] MORPHOLINE COMPOUNDS AND METHOD OF PROMOTING ANIMAL GROWTH

[76] Inventors: Aldo Garzia, Viale Delle Rimembranze, 2 Lodi (Milano); Umberto Bucci, Via Pantano, 5 Milano, both of Italy

[21] Appl. No.: 111,656

[22] Filed: Oct. 23, 1987

Related U.S. Application Data

[63] Continuation of Ser. No. 3,256, Jan. 14, 1987, abandoned.

[30] Foreign Application Priority Data

Jan. 27, 1986 [IT] Italy .............................. 19196 A/68

[51] Int. Cl.$^4$ .................. A61K 31/535; C07D 295/18
[52] U.S. Cl. .................................. 514/231.5; 544/148
[58] Field of Search ........................ 544/148; 514/238

[56] References Cited

U.S. PATENT DOCUMENTS 2,830,988  4/1958  Scheffler et al. ..................... 544/148
4,115,570  9/1978  Garzia ............................. 544/174

Primary Examiner—Robert W. Ramsuer
Attorney, Agent, or Firm—Bernard, Rothwell & Brown

[57] ABSTRACT

There are disclosed compounds of the formula

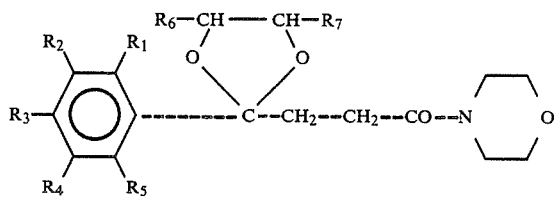

wherein $R_1$, $R_2$, $R_3$, $R_4$ and $R_5$, which can be the same or different, are each selected from hydrogen, alkyl of 1 to 4 carbon atoms and alkoxy of 1 to 4 carbon atoms; and $R_6$ and $R_7$, which can be the same or different, are each selected from hydrogen and alkyl 1 to 3 carbon atoms. The compounds are useful as growth promoting agents in animals.

6 Claims, No Drawings

MORPHOLINE COMPOUNDS AND METHOD OF PROMOTING ANIMAL GROWTH

This is a continuation of application Ser. No. 003,256, filed Jan. 14, 1987, now abandoned.

BACKGROUND OF THE INVENTION

This invention relates to morpholine derivatives and, more specifically, the a γ-phenyl-γ-1,3-(4-methyl)-dioxolan-butyric acid amide, the method of its preparation, its use as a growth stimulant in animals, and improvement of feed-utilization.

It is an objective of the meat production industry to stimulate the growth of animals and to improve utilization of feed. It is known that agents with estrogenic activity can be used for this purpose; these agents, however, have been banned recently by numerous countries because they sometimes produce serious side effects.

Various other agents, or groups of agents, are currently being used as growth promoters in a number of animal species. For the rearing of swine, for example, quinoxalines are used, as described by Haddadin et al. (British Patent No. 1,305,138), by A. Garzia and R. D. Williams (U.S. Pat. No. 4,128,642) and others. U.S. Pat. No. 3,232,345 to Hodge et al. discloses the use of zearalanol as a growth-promoting agent in cattle and sheep. Bacitracin derivatives are used as growth-promoting agents in chickens.

Where the quinoxalines, the antibiotics, and their derivatives are concerned, most of the growth stimulating action is based on the health status of the treated animals and this treatment does not provide for improvement of the diet-conversion factor. Furthermore, these compounds cause environmental ecological problems. Currently used anabolic agents are known to act by means of an undesirable hormonal function.

Another disadvantage of currently used growth stimulants is that they frequently are active only in limited species, in some cases only in a single animal species. Frequently, they do not provide for improvement of conversion of food into meat.

There is still a need for agents which stimulate the growth of animals without the disadvantages associated with presently used products, and which can be used in several animal species with satisfactory results.

SUMMARY OF THE INVENTION

In accordance with the invention, there are provided morpholine derivatives, specifically, cyclic amides of γ-phenyl-γ-1,3-dioxolan butyric acids. There is also provided a method for their preparation. The compounds of the invention are useful as growth promoters in various animal species.

The preferred compound is a γ-phenyl-γ-1,3-(4-methyl)-dioxolanbutyric acidamide obtained by reacting β-benzoylpropionic acid morpholinamide with 1,2-propylene glycol in the presence of p-toluenesulfonic acid.

DESCRIPTION OF THE INVENTION

We have found that the cyclic γ-phenyl-γ-1,3-dioxolan butyric acid amides of the invention are capable of stimulating growth factors in several animal species without exhibiting hormonal or chemotherapeutic activities, and without causing ecological problems. The subject compounds also exhibit anti-stress-activity. The compounds exhibit very low toxicity.

They are metabolized rapidly and the metabolites have minimal toxicity.

The compounds of the invention have the general formula I.

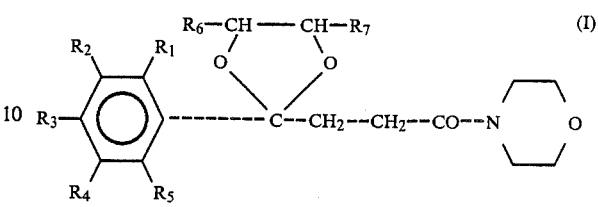

wherein $R_1$, $R_2$, $R_3$, $R_4$ and $R_5$, which can be the same or different, are each selected from hydrogen, alkyl from 1 to 4 carbon atoms and alkoxy from 1 to 4 carbon atoms; and $R_6$ and $R_7$, which can be the same or different, are each selected from hydrogen and alkyl from 1 to 3 carbon atoms.

The compounds are obtained by the reaction of β-benzoylpropionic acid morphonylamide with 1,2-glycols such as ethylene glycol, propylene glycol, etc. The rection is preferably carried out in a suitable solvent such as benzene at boiling temperature for about 50 hours, in the presence of a catalyst such as p-toluenesulfonic acid monohydrate. The presence of a large excess of glycol is essential, and the reaction is facilitated by removal of the water formed while the reaction is in process.

The preferred compound of the invention is a γ-phenyl-γ-1,3-(4-methyl)-dioxolanbutyric acid amide with the formula II.

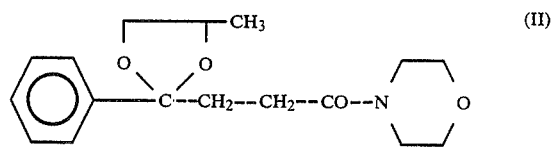

This compound is obtained by treating a quantity (equivalent) of amide with a 20-30 fold excess of propylene glycol in a quantity of benzene equal to a 4-8 fold volume of the propylene glycol. The reaction is carried out in the presence of a small quantity of p-toluenesulfonic acid monohydrate, at reflux for 50 hours with azeotropic distillation of the water formed during the reaction.

In a number of tests, the toxicity of the compound of formula II was found to be extremely low in relation to the "dosage" that was used: the $LD_{50}$ in the mouse for i.p. administration is 565 mg/kg, while the p.o. toxicity is 955 mg/kg.

A dosage of 100 mg/kg, i.p., has a sedative action in the rat. Upon administration in rats, we observed a significant increase of the β-endorphin level in the left nucleus; this is believed to be the cause of the growth stimulating activity since the relation between increased β-endorphin levels and the production of growth hormone is well known.

The compound of the invention is administered to animals to promote growth. The compound is capable of stimulating the desire for food in the treated animals, and producing a better feed-conversion index in cattle, swine, horses, sheep, and chickens. The ratio for meat/fat/bone remains unchanged in animals treated with the compound. The animals are treated by i.m. injection or p.o. administration with food, or by implantation. Advantageously, solutions of 2% in propylene glycol are used for injections, with each animal receiving 2.5–1.0 mg/kg active component.

Injections are administered when treatment is initiated, after about 15 days, and again after about 30 days. On day 60, compared to the controls, the status of nutrition is equivalent to that of untreated controls receiving the same diet, while there is a 12–15% weight increase compared to the controls. These results were obtained in cattle, swine, horses, sheep, rodents, and chickens.

P.o. treatment allows the use of about a 10-times higher dose of the active component. The compound is mixed daily with the diet for a total of about 30 days.

Treatment with the compound of the invention dose not preclude—and is compatible with—drug therapy, e.g., antibiotics, vitamins, etc.

The treated animals are specifically resistant to stress during transport, changes in weather, or stabling.

The following examples are intended to illustrate further the practice of the invention and are not intended to limit its scope in any way.

EXAMPLE I

Preparation of Compound for Formula II 24.7 g β-benzoyl propionic acid morpholinamide (0.1 mole) were boiled at reflux for 50 hours with 500 mL anhydrous benzene, 70 mL 1,2-propylene glycol, and 0.5 g p-toluenesulfonic acid monohydrate with stirring, using a water separator.

The reaction mixture was then evaporated to ⅓ of the initial volume at reduced pressure and poured into about 100 g cracked ice. The organic layer was separated and cooled to about 10° C. after further evaporation. After standing overnight at about 10° C., 22.0 g product were obtained by centrifugation and after drying in vacuo (yield, 70% of the theoretical).

The product had the appearance of a wax, and both the N.M.R. and I.R. spectra confirmed the anticipated structure. The compound was soluble in methanol, ethanol, benzene, glycols and D.M.F.

EXAMPLE II i.m. Treatment of Cattle

A total of 10 bulls, mean weight 500 kg, were treated i.m. with 10 mL of a 2% solution of compound II, and fed the same diet as 10 other bulls with the same weight, serving as controls. Treatment was repeated on day 15 from initiation, and repeated once again on day 30. The animals were weighed on day 60 indicating a weight 13% higher than that of the controls. When the animals were butchered, the organs of the treated animals did not indicate any abnormalities; the ratio of meat-to-fat remained unchanged.

What is claimed is:

1. A compound of the formula

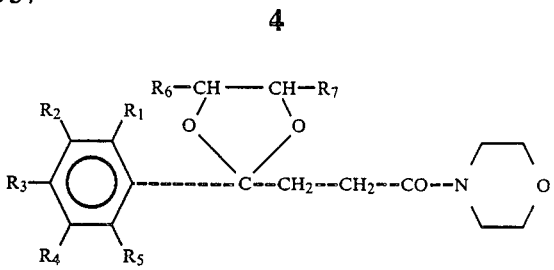

wherein $R_1$, $R_2$, $R_3$, $R_4$ and $R_5$, which can be the same or different, are each selected from hydrogen, alkyl of 1 to 4 carbon atoms and alkoxy of 1 to 4 carbon atoms; and $R_6$ and $R_7$, which can be the same or different, are each selected from hydrogen and alkyl 1 to 3 carbon atoms.

2. The compound of the formula

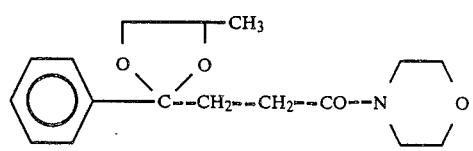

3. A method of promoting the growth of an animal which comprises administering to the animal a growth-promoting amount of a compound of the formula

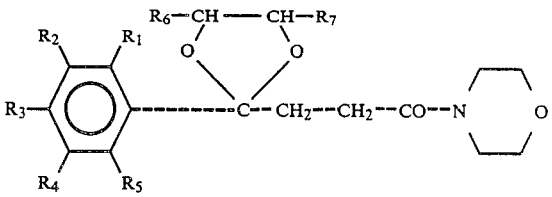

wherein $R_1$, $R_2$, $R_3$, $R_4$ and $R_5$, which can be the same or different, are each selected from hydrogen, alkyl of 1 to 4 carbon atoms and alkoxy of 1 to 4 carbon atoms; and $R_6$ and $R^7$, which can be the same or different, are each selected from hydrogen and alkyl 1 to 3 carbon atoms.

4. A method as claimed in claim 3 wherein the compound has the formula

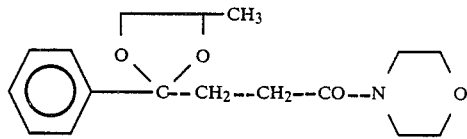

5. A method as claimed in claim 3 wherein the compound is administered orally.

6. A method as claimed in claim 3 wherein the compound is administered by injection.

* * * * *